United States Patent

Mendoza

[11] Patent Number: 5,405,265
[45] Date of Patent: Apr. 11, 1995

[54] DENTAL PROPHYLAXIS CUP

[75] Inventor: Jose L. Mendoza, Rancho Cordova, Calif.

[73] Assignee: Denticator International, Inc., Rancho Cordova, Calif.

[21] Appl. No.: 100,629

[22] Filed: Jul. 30, 1993

[51] Int. Cl.⁶ ............................................. A61C 3/06
[52] U.S. Cl. ...................................................... 433/166
[58] Field of Search ................................. 433/125, 166

[56] References Cited

U.S. PATENT DOCUMENTS

| | | | |
|---|---|---|---|
| Re. 24,391 | 11/1957 | McFadden | 51/170 T |
| 263,814 | 9/1882 | Schmitz | 433/112 |
| 1,999,488 | 4/1935 | Swisher | 433/128 |
| 2,017,881 | 10/1935 | Wiseman | 433/166 |
| 2,025,779 | 12/1935 | Roelke | 433/128 |
| 2,135,933 | 11/1938 | Blair | 433/166 |
| 2,226,145 | 12/1940 | Smith | 433/166 |
| 2,300,828 | 11/1942 | Goldenberg | 433/166 |
| 2,315,016 | 3/1943 | Shotton | 433/133 |
| 2,328,270 | 8/1943 | Greenberg | 74/56 |
| 2,789,352 | 4/1957 | Wiseman | 433/166 |
| 2,937,444 | 5/1960 | Kern | 433/132 |
| 3,163,934 | 1/1965 | Wiseman | 433/115 |
| 3,192,922 | 7/1965 | Winkler | 128/62 A |
| 3,229,369 | 1/1966 | Hoffmeister | 433/126 |
| 3,421,224 | 1/1969 | Brehm | 433/132 |
| 3,727,313 | 4/1973 | Graham | 433/125 |
| 3,740,853 | 6/1973 | Brahler | 433/124 |
| 3,855,704 | 12/1974 | Booth | 433/101 |
| 3,877,574 | 4/1975 | Killick | 206/368 |
| 3,955,284 | 5/1976 | Balson | 433/132 |
| 3,987,550 | 10/1976 | Danne | 433/133 |
| 4,053,983 | 10/1977 | Flatland | 433/133 |
| 4,182,041 | 1/1980 | Girard | 433/115 |
| 4,248,589 | 2/1981 | Lewis | 433/80 |
| 4,259,071 | 3/1981 | Warden | 433/166 |
| 4,266,933 | 5/1981 | Warden | 433/82 |
| 4,365,956 | 12/1982 | Bailey | 32/59 |
| 4,693,871 | 9/1987 | Geller | 433/116 |
| 4,795,343 | 1/1989 | Choisser | 433/116 |
| 4,842,516 | 6/1989 | Choisser | 433/132 |
| 4,929,180 | 5/1990 | Moreschini | 433/166 |
| 4,941,828 | 7/1990 | Kimura | 433/114 |
| 5,020,994 | 6/1991 | Huang | 433/126 |
| 5,028,233 | 7/1991 | Witherby | 433/125 |
| 5,040,978 | 8/1991 | Falcon | 433/125 |
| 5,094,615 | 3/1992 | Bailey | 433/88 |
| 5,120,220 | 6/1992 | Butler | 433/125 |
| 5,156,547 | 10/1992 | Bailey | 433/125 |

FOREIGN PATENT DOCUMENTS 646193 6/1937 Germany .
2209284 10/1989 United Kingdom .

OTHER PUBLICATIONS

Advertisement for *Smart Angle* from a company called SmartPractice in Phoenix, Ariz.

*Primary Examiner*—Cary E. O'Connor
*Attorney, Agent, or Firm*—Bernhard Kreten

[57] ABSTRACT

A dental prophylaxis cup (10) is provided. The cup (10) is rotatably attachable to prophy angles (D) and hence to a dental handpiece. An interior (60) of the prophylaxis cup (10) includes a sidewall (62) extending upwardly and outwardly from a floor (64) of the interior (60) to a rim (50) at a top of the prophylaxis cup (10). The side wall (62) includes projections (70) extending therefrom. Each projection (70) completely surrounds a confinement region (73). Adjacent projections (70) are spaced apart by a gap (78). The gap (78) defines an upper end of an impoundment region (80) located between the floor (64) and confinement regions (73), separated therefrom by projections (70). Polishing compound is retained within the confinement region (73) and impoundment region (80) either until sufficient force (P) is applied, or the cup (10) is distorted, causing the polishing compound to migrate toward the rim (50).

21 Claims, 3 Drawing Sheets

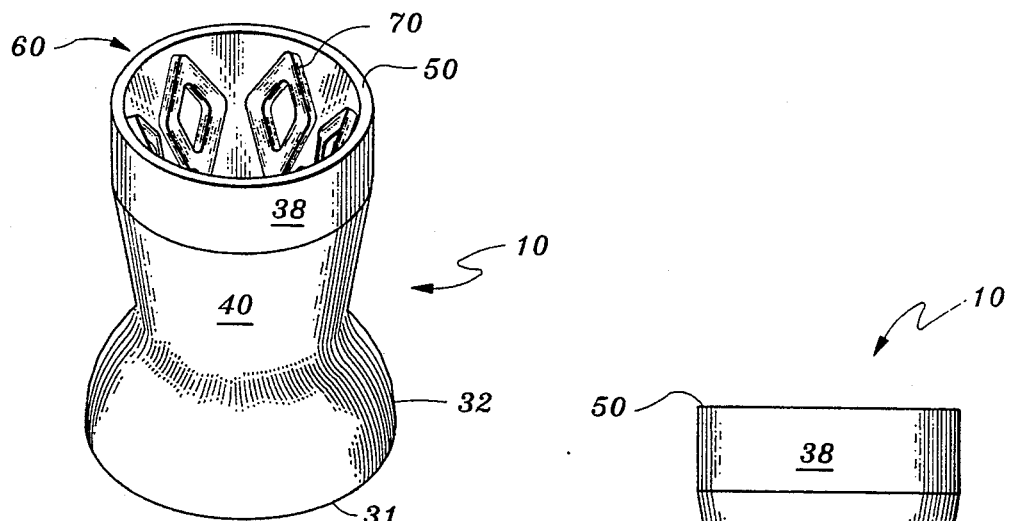
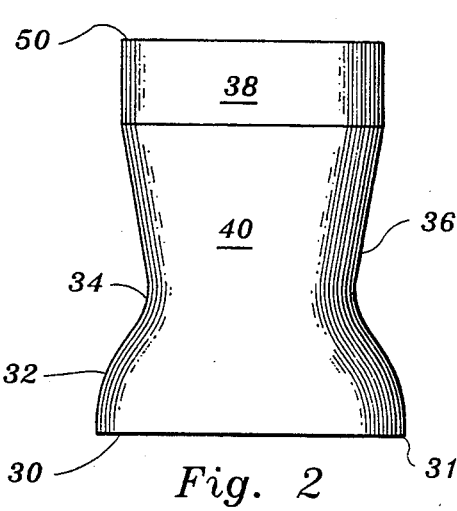
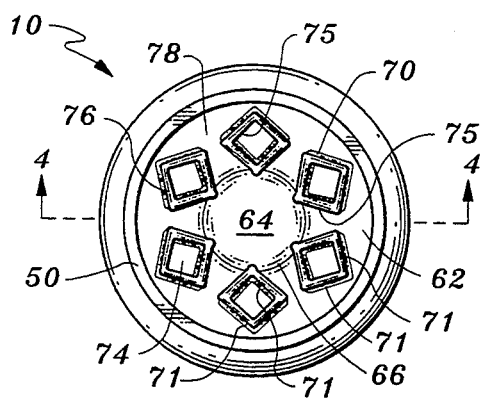
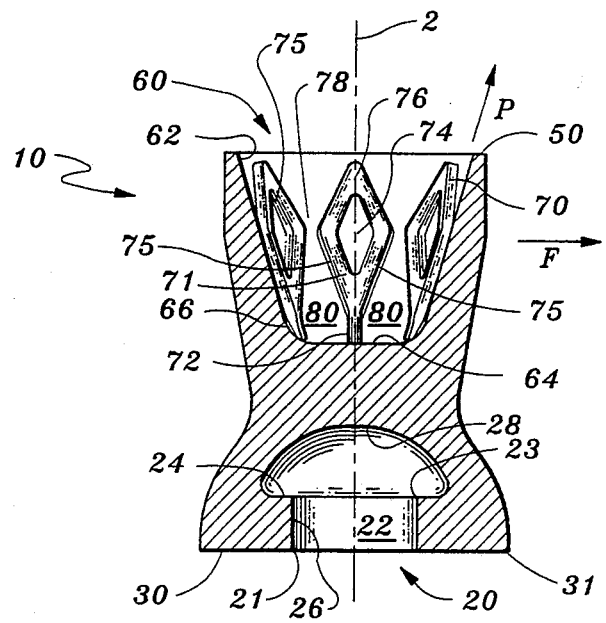

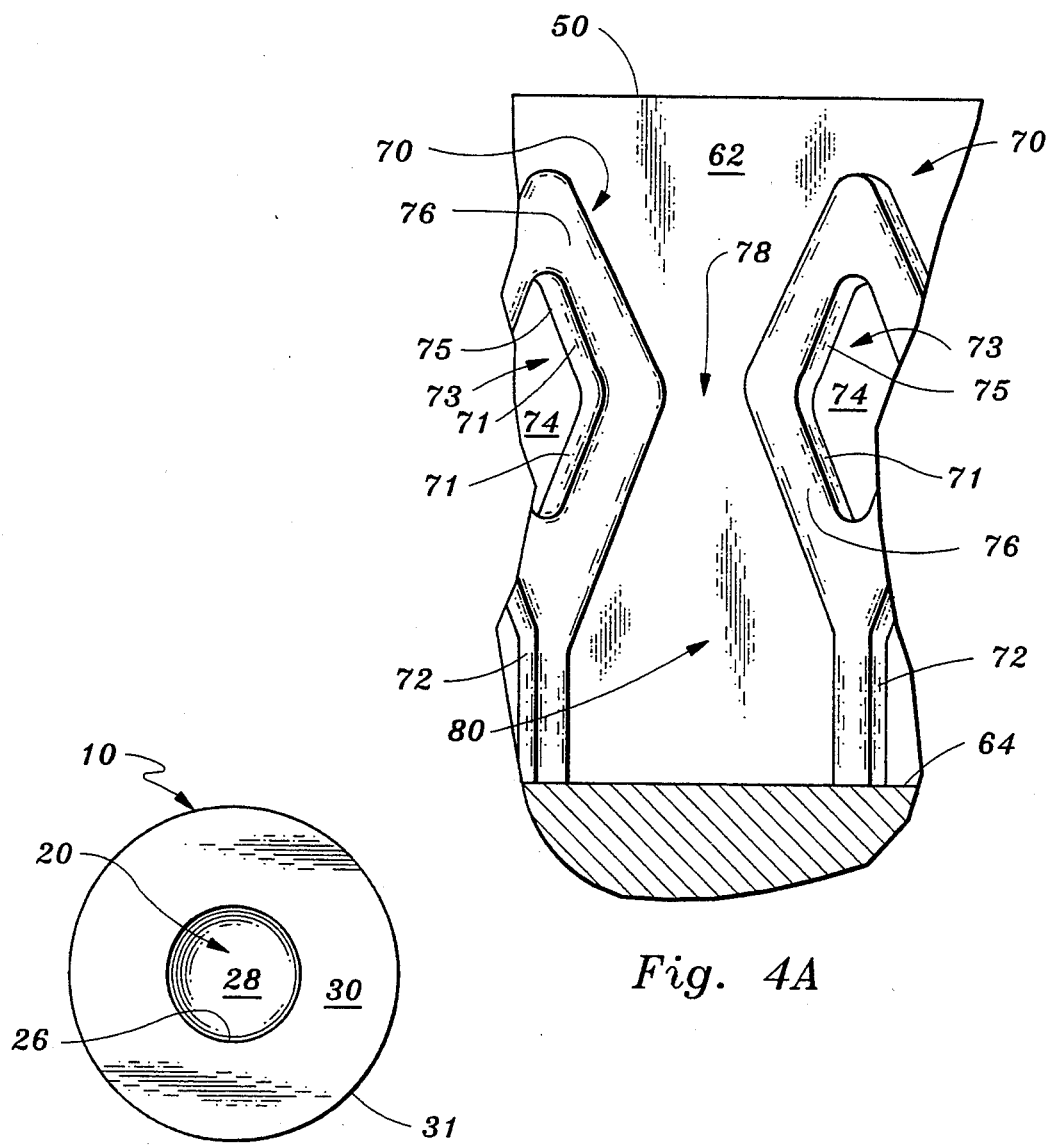
Fig. 4A
Fig. 5
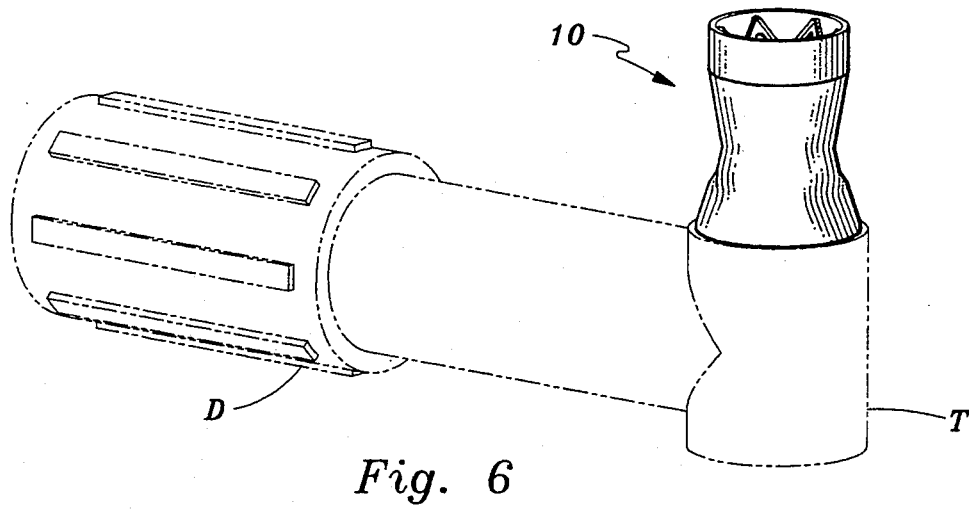
Fig. 6

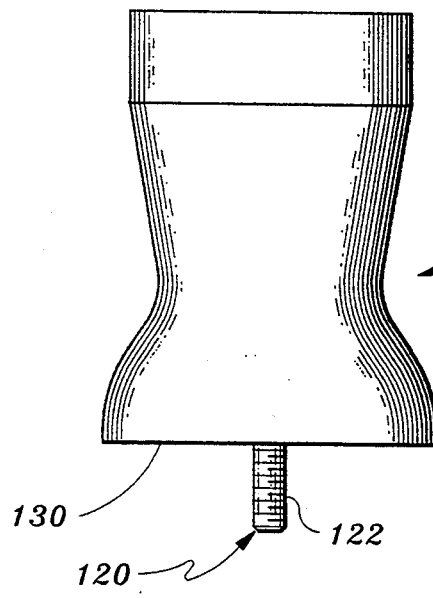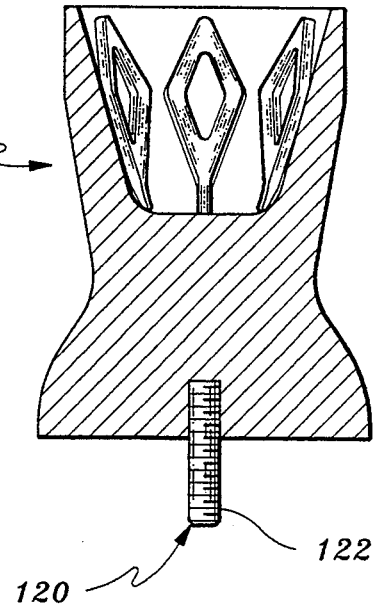
Fig. 7          Fig. 8
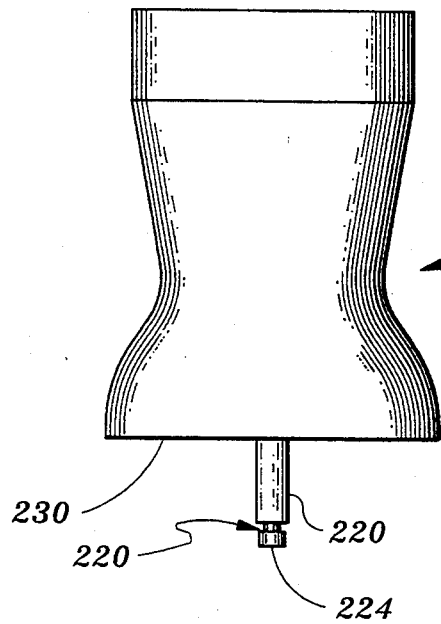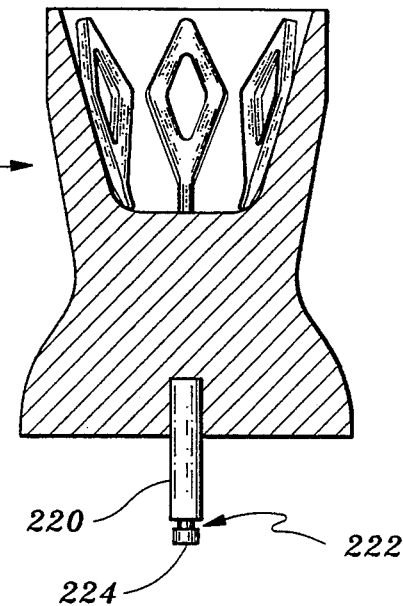
Fig. 9          Fig. 10

DENTAL PROPHYLAXIS CUP

FIELD OF THE INVENTION

The following invention is related to tools for polishing dental structures such as teeth. More specifically, this invention relates to dental prophylaxis cups removably attachable to a prophy angle attachment of a dental handpiece. The cups include projections on an interior which restrain polishing compound from rapidly exiting the interior when the prophylaxis cup is rotated.

BACKGROUND OF THE INVENTION

Disposable prophy angles, such as that described in detail in U.S. Pat. No. 3,727,313, are utilized in conjunction with a dental handpiece to perform dental prophylaxis and polish teeth and other dental structures. Prophylaxis is actually performed by a flexible attachment to the tip of the prophy angle called a prophylaxis cup or prophy cup. These prophy cups can be attached to either disposable or nondisposable prophy angles. In either case, the prophy cup includes one end attached through the prophy angle to the dental handpiece and a second end for receiving and applying polishing compound to clean the teeth and other dental structures. The cup rotates at the control of the dental practitioner through a drill mechanism contained in the handpiece and prophy angle.

The second end of a prophy clip includes an interior that is a generally concave depression with sidewalls that diverge conically outwardly as the sidewalls extend away from a floor of the interior. Vanes are often attached to the sidewalls which extend from the floor to a rim of the concave interior. Most vanes extend in a plane which passes through an axis of rotation of the prophy cup.

During prophylaxis, the dental professional typically fills the cup with polishing compound and applies some of the polishing compound to the teeth to be cleaned before initiating rotation of the cup. The handpiece is then activated, causing the cup to spin about its axis of rotation and the prophy cup is moved over surfaces of the dental structures with the sidewalls of the interior flexing upon contact with surfaces of the dental structures. The vanes assist in the cleaning process by applying additional pressure to the polishing compound and the dental structures.

While these vanes have proven satisfactory in cleaning the dental structures, these vanes have proven particularly ineffective in retaining the polishing compound within the concave depression immediately prior to contacting the teeth. This is especially true because rotation of the cup is typically initiated before the polishing compound in the cup contacts the dental structures. When the cup is rotated, any polishing compound within the interior of the prophy cup is urged by centrifugal forces to migrate from the interior. As is known, centrifugal force is perpendicular to the axis of rotation. However, because the sidewalls of the concave depression of the interior are sloped outwardly, a component of that centrifugal force is directed out of the interior along the face of the sidewall. The vanes, being oriented in planes which pass through the axis of rotation, fail to inhibit this motion of the polishing compound out of the interior. As a result, the polishing compound is often flung prematurely out of the cup, wasting the compound and creating a mess.

This problem makes maintenance of a clean environment surrounding the patient more difficult. Furthermore, patient discomfort is often increased because greater amounts of polishing compound are ingested by the patient. Also, the prophylaxis operation is slowed significantly in that the dental practitioner must repeatedly fill the prophy cup with additional polishing compound. Accordingly, a need exists for a prophy cup which tends to retain polishing compound therein until the prophy cup impacts the teeth and dental structures to be cleaned, even when the prophy cup is rotating.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| PATENT NO. | ISSUE DATE | INVENTOR |
|---|---|---|
| 263,814 | 09/1882 | Schmitz |
| 1,999,488 | 04/1935 | Swisher |
| 2,025,779 | 12/1935 | Roelke |
| 2,135,933 | 11/1938 | Blair |
| 2,300,828 | 11/1942 | Goldenberg |
| 2,315,016 | 03/1943 | Shotton |
| 2,328,270 | 08/1943 | Greenberg |
| Re. 24,391 | 11/1957 | McFadden |
| 2,937,444 | 05/1960 | Kern |
| 3,163,934 | 01/1965 | Wiseman |
| 3,192,922 | 07/1965 | Winkler |
| 3,229,369 | 01/1966 | Hoffmeister |
| 3,421,224 | 01/1969 | Brehm |
| 3,727,313 | 04/1973 | Graham |
| 3,740,853 | 06/1973 | Brahler |
| 3,855,704 | 12/1974 | Booth |
| 3,877,574 | 04/1975 | Killick |
| 3,955,284 | 05/1976 | Balson |
| 3,987,550 | 10/1976 | Danne |
| 4,053,983 | 10/1977 | Flatland |
| 4,182,041 | 01/1980 | Girard |
| 4,248,589 | 02/1981 | Lewis |
| 4,259,071 | 03/1981 | Warden |
| 4,266,933 | 05/1981 | Warden |
| 4,365,956 | 12/1982 | Bailey |
| 4,693,871 | 09/1987 | Geller |
| 4,795,343 | 01/1989 | Choisser |
| 4,842,516 | 06/1989 | Choisser |
| 4,929,180 | 05/1990 | Moreschini |
| 4,941,828 | 07/1990 | Kimura |
| 5,020,994 | 06/1991 | Huang |
| 5,028,233 | 07/1991 | Witherby |
| 5,040,978 | 08/1991 | Falcon |
| 5,094,615 | 03/1992 | Bailey |
| 5,120,220 | 06/1992 | Butler |
| 5,156,547 | 10/1992 | Bailey |
| FOREIGN PATENT DOCUMENTS | | |
| 646,193 German | 06/1937 | Dürhager |
| GB 2,209,284 A | 10/1989 | Kimura |
| OTHER PRIOR ART | | |

Advertisement for Smart Angle, SmartPractice, Phoenix, AZ
Denticator brochure, Rancho Cordova, California, 1990, entire brochure The patents to Warden and Moreschini teach the use of a prophy cup with ridges on an interior surface. This invention is distinguishable from Warden and Moreschini in that, inter alia, the projections of this invention are not biased to draw polishing compound toward a floor of the interior, but rather merely act to inhibit polishing compound migration away from the floor. Also, different regions within the interior of this invention provide varying magnitudes of restraint, allowing the polishing compound to escape the interior in a controlled, consistent manner over a longer time period.

SUMMARY OF THE INVENTION

This invention provides a prophy cup attachable to a prophy angle and hence operatively coupled to a rotational input from a dental handpiece. The prophy cup includes a bottom surface typically with an orifice therein designed to readily attach to a shaft output of the prophy angle near the tip of the prophy angle. The prophy cup extends up from the bottom surface to a waist defining a narrowest diameter portion, along a slope which diverges outwardly from a central axis, and then up to a rim. The rim defines a perimeter of an interior which is essentially a concave depression including a sidewall extending up from a floor.

The sidewall of the interior includes projections thereon. The projections include multiple line segments that are spaced such that groups of line segments combine to form recesses totally bounded by the line segments. The recesses define confinement regions for the polishing compound. Adjacent projections are spaced slightly apart by gaps therebetween. The line segments of each projection are oriented at angles which are non-coplanar with a central axis of the prophy cup. The central axis is coextensive with an axis of rotation of the prophy cup and an axis about which the prophy cup is radially symmetrical. Below each gap is located an impoundment region which is bounded by the floor, line segments of adjacent projections and the gap.

The impoundment region defines an area where polishing compound can be stored and then subsequently migrate along the sidewall toward the rim when the prophy cup is rotating, but the polishing compound's migration is restricted and impeded somewhat by the gap. The confinement region defines an area which retains the polishing compound and restricts the polishing compound from migrating along the sidewall toward the rim unless the polishing compound climbs over the projection surrounding the confinement region or the walls of the cup flex so that the dental structures touch the area. By orienting the projections to have live segments that are not coplanar with the central axis of the prophy cup, the projections include resistance sides that resist motion of the polishing compound along the sidewall toward the rim. The polishing compound thus tends to be held within the interior of the prophy cup until it is dislodged by impact with dental structures.

OBJECTS OF THE INVENTION

Accordingly, it is the primary object of the present invention to provide a prophy cup which restrains polishing compound located in the interior thereof from uncontrolled exiting the prophy cup under centrifugal force.

Another further object of the present invention is to provide a prophy cup which is easily attachable to and removable from a prophy angle.

Another object of the present invention is to provide a prophy cup which is highly elastic and deformable to conform to the shapes of dental structures to be polished.

Another object of the present invention is to provide a prophy cup which prevents the polishing compound from being displaced and wasting the polishing compound.

Another object of the present invention is to provide a prophy cup which more comfortably polishes the dental structures of the patient.

Another further object of the present invention is to provide a prophy cup which saves a dental professional time in polishing dental structures of the patient.

Another further object of the present invention is to provide a prophy cup which includes distinct regions having various degrees of metering of polishing compound outward therefrom, thereby spreading out the rate of deposition of polishing compound out of the prophy cup and onto the dental structures.

Another further object of the present invention is to provide a prophy cup which lends itself to low-cost manufacture from low-cost materials.

Another further object of the present invention is to provide a prophy cup which is readily attachable to a rotational output shaft.

Viewed from a first vantage point, it is an object of this present invention to provide a dental prophylaxis cup for applying polishing compound to dental structures which includes: a cup having a bottom surface on a first end including an attachment means, and a second end opposite the first end including a concave interior region defined by a sidewall extending from a floor to a rim; and a plurality of projections extending from the sidewall, the projections including means for restraining release of polishing compound from within said interior region.

Viewed from a second vantage point, it is an object of this present invention to provide a dental prophylaxis polishing compound dispensing device which is removably connected to a dental handpiece, the device includes: a cup having an attachment end and a dispensing end, the attachment end including means for attaching to the dental handpiece in a rotatably supportable manner, such that rotational force supplied by the dental handpiece is transmitted to the cup, and a polishing compound retention surface upon said dispensing end, the retention surface including means to resist centrifugal force applied to the polishing compound by rotation of the cup; whereby when polishing compound is applied to the retention surface and the cup is rotated, the retention surface resists release of the polishing compound.

Viewed from a third vantage point, it is an object of this present invention to provide a method for applying polishing compound to dental structures of an individual and polishing the dental structures, including the steps of: providing a prophy cup having an attachment end attachable to a prophy angle, the prophy angle in turn attachable to a dental handpiece in a manner supplying rotation from the dental handpiece to the cup, and a dispensing end with a polishing compound retention surface; filling the dispensing end of the prophy cup with polishing compound; applying a portion of the polishing compound remote from the retention surface to the dental structure to be polished; rotating the prophy cup; polishing the dental structure with the dispensing end of the prophy cup; and metering flow of a portion of the polishing compound, adjacent the retention surface, into contact with the dental structures; whereby polishing compound is provided within the prophy cup for an extended period of time without repeating said filling step.

BRIEF DESCRIPTION OF THE DRAWINGS

FIG. 1 is a prospective view of the prophylaxis cup of this invention.

FIG. 2 is a side view of that which is shown in FIG. 1.

FIG. 3 is a top view of that which is shown in FIG. 1.

FIG. 4 is a sectional view taken along line 4—4 of FIG. 3.

FIG. 4A is a detail of a portion of that which is shown in FIG. 4.

FIG. 5 is the bottom view of that which is shown in FIG. 1.

FIG. 6 is a prospective view of the prophylaxis cup of this invention in place upon a disposable prophy angle.

FIG. 7 is an elevational view of an alternative embodiment of the prophy clip.

FIG. 8 is a full section view of that which is shown in FIG. 7.

FIG. 9 is an elevational view of an alternative embodiment of the prophy cup.

FIG. 10 is a full section view of that which is shown in FIG. 9.

DESCRIPTION OF PREFERRED EMBODIMENTS

Referring to the drawings, wherein like reference numerals represent like parts throughout, reference numeral 10 is directed to a prophy cup (FIGS. 1 through 5) for use in applying polishing compound to teeth and other dental structures. The prophy cup 10 is attachable to a tip T of a prophy angle D (FIG. 6) in a manner which is operatively connected to a rotational shaft coupled to a dental handpiece.

In essence, the prophy cup 10 is a unitary mass formed from flexible elastomeric material. The prophy cup 10 includes a bottom surface 30 on a first end with an orifice 20 therewithin. The orifice 20 is shaped complemental to a drive protuberance of the prophy angle D so that the bottom surface 30 is attached to the prophy angle D. An exterior 40 of the prophy cup 10 includes a hip 32 adjacent the bottom surface 30 that extends upward into a waist 34. The waist 34 then extends upward and outwardly along a slope 36 to a cylindrical collar 38. The collar 38 includes a rim 50 at an upper side of the collar 38.

The rim 50 is located on a second end of the prophy cup 10 and surrounds an interior 60 of the prophy cup 10 which includes a sidewall 62 extending between the rim 50 and a floor 64. The sidewall 62 includes projections 70 thereon. Each projection 70 includes a confinement region 73 surrounded by the projection 70. Gaps 78 are formed between adjacent projections 70. Impoundment regions 80 are formed below each gap 78 and between adjacent projections 70. The projections 70 include resistance sides 75 below a crest 76 of each projection 70. Projections of the resistance sides 75 define planes which are not coplanar with a central axis 2 of the prophy cup 10. The projections 70 provide a means for restraining release of polishing compound and encourages polishing compound to remain in the interior 60 of the prophy cup 10 even when the prophy cup 10 is rotating about the central axis 2.

More specifically, and with reference to FIGS. 4 and 5, the orifice 20 located at the bottom surface 30 is substantially mushroom shaped and includes a neck 22 formed as a cylindrical surface 26 between a lower edge 21 and an upper edge 23. The lower edge 21 demarcates a circular 90° transition between the planar bottom surface 30 and the cylindrical surface 26 of the neck 22. The upper edge 23 is also circular and demarcates a 90° transition into a shelf 24. The shelf 24 is a substantially planar circular surface parallel to the bottom surface 30 and surrounding the neck 22. A concave domed surface 28 extends over the shelf 24 and has a perimeter which transitions into an outer edge of the shelf 24 via a smooth radius. The neck 22 thus provides a lesser width passage into a greater width region below the concave surface 28.

The prophy cup 10 is formed from sufficiently flexible material to allow a protuberance of the prophy angle D, having a contour complemental to the orifice 20, to distend and pass through the neck 22 and above the shelf 24 of the orifice 20. In this way, the protuberance is locatable within the orifice 20 securely connecting the prophy cup 10 to the prophy angle D. The bottom surface 30 provides an attachment end of the prophy clip 10 which is opposite a dispensing end of the prophy cup 10.

Referring now to FIGS. 1, 2 and 4, the bottom surface 30 is a substantially planar circular surface having an outer periphery defined by a circular edge 31. The exterior 40 of the prophy cup 10 extends from the edge 31 up to the rim 50 and has an irregular surface contour. However, the exterior 40 is substantially radially symmetrical about a central axis 2 perpendicular to the bottom surface 30.

The exterior 40 includes a hip 32 located along a lower one-third of the prophy cup 10 from the edge 31. The hip 32 has an initially greater diameter curvedly transitioning into a lesser diameter at a waist 34 located above the hip 32. The waist 34 defines a least diameter portion of the exterior 40. The waist 34 then transitions into a substantially linear slope 36 which extends upwardly and outwardly toward the rim 50. The slope 36 transitions into a collar 38 which is a substantially cylindrical surface with an upper extremity defining the rim 50. The exterior 40 of the prophy cup 10 can alternatively have a variety of configurations so long as the bottom surface 30 of the prophy cup 10 is sized and shaped properly to interface with a prophy angle D or other appropriate rotational shafts and so long as the rim 50 is sized appropriately to effectively polish teeth and other dental structures.

Referring now to FIGS. 1, 3 and 4, the rim 50 defines an upper extent of an interior 60 of the prophy cup 10. The interior 60 is substantially a concave depression defined by a sidewall 62 extending between the rim 50 and a floor 64. The rim 50 has a diameter greater than a diameter of the floor 64. The sidewall 62 can have a linear contour such that the sidewall 62 defines a frustum with a greater diameter portion near the rim 50 and the lesser diameter portion near the floor 64. Alternatively, the sidewall 62 may display a somewhat curved contour only generally approximating that of a frustum. The sidewall 62 transitions to the floor 64 with a curving corner 66.

The interior 60 provides a region into which polishing compound can be placed for polishing teeth and other dental structures. The cup 10 is thin near the top. Thus, the sidewall 62 is preferably spaced only a small distance from the slope 36 of the exterior 40. In this way, the sidewall 62 of the interior 60 can be easily deformed causing the sidewalls 62 to exhibit different angles of divergence with respect to the central axis 2 when loaded in various ways.

The sidewall 62 supports a plurality of projections 70 extending substantially perpendicularly therefrom. Each projection 70 preferably is formed from a series of line segments and a leg 72. The leg 72 extends upward from the floor 64 along the sidewall 62 and toward the rim 50. The leg 72 transitions into line segments 71 preferably configured in a diamond-like shape surrounding a recess 74. The line segments 71 can also be formed into other polygonal structures resulting in various slightly different multi-faceted recesses. Also, the line segments 71 could be curved to allow the recess 74 to more closely approximate a circle or other curve sided region. The recess 74 has a depth similar to a height of the projections 70 surrounding the recess 74. Each projection 70 is spaced from adjacent projections 70 somewhat so that a gap 78 is formed between adjacent projections 70.

When the projections 70 are observed in combination, as shown in detail in FIG. 4A, confinement regions 73 are defined by the recess 74 providing an open top enclosure which is circumscribed by the projection 70. Also, impoundment regions 80 are defined between adjacent projections 70, above the floor 64 and below the gaps 78 formed between adjacent confinement regions 73. The confinement regions 73 are characterized by being entirely surrounded by line segments 71 of a projection 70. Alternatively, the confinement regions 73 could only be surrounded by line segments 71 on a side closest to the rim 50, preventing migration toward the rim 50. The impoundment regions 80 are characterized by being surrounded on two sides by projections 70 and the legs 72 extending therefrom, on one side by the floor 64 and on one side by the gap 78. The legs 72 segregate adjacent impoundment regions 80 from each other.

Each projection 70 includes a crest 76 defining a highest portion of the projections 70 above the sidewall 62. The projections 70 are oriented with the line segments 71 each oriented in a plane non-coplanar with the central axis 2. The legs 72 of each projection 70 then extend downward from the line segments 71 to the floor 64 within a plane coplanar with the central axis 2. The line segments 71 of the projections 70 have a resistance side 75 extending from the sidewall 62 to the crest 76 that faces the floor 64 more directly than it faces the rim 50.

Each line segment 71 of each projection 70 preferably extends substantially linearly along a line that is skewed with respect to the central axis 2 and does not intersect the central axis 2. Also, the line segments 71 are not parallel to the central axis 2. Some line segments 71 are oriented non-parallel with adjacent line segments 71. Thus, adjacent line segments 71 have varying separation distances along their lengths. Structures resembling constricting funnels and bottlenecks are formed as a result. Thus, each line segment 71 has one side forming the resistance side 75 and an opposite side which faces the rim 50 somewhat. The projections 70 on the sidewall 62 allows the sidewall 62 to function as a retention surface, impeding the polishing compound from migrating toward the rim 50. Alternatively, the line segments 71 could have a somewhat curved structure.

While the projections 70 shown in FIGS. 1, 3 and 4 represent one form of a means to resist centrifugal force within the interior 60, other structures are also contemplated. For instance, concentric projections could extend from the sidewalls 62 in planes parallel to the floor 64. Also, projections could spiral helically from the floor 64 to the rim 50 in a criss-crossing manner. Dimples or other surface irregularities could also provide the force resistance means.

In use and operation, the prophy cup 10 and especially the projections 70 function in the following manner. Initially, polishing compound is located within the interior 60 of the prophy cup 10. This polishing compound is generally characterized by having a specified grit and viscosity. The viscosity of the polishing compound is generally high but diminishes with exposure to water and other liquids such as saliva. Thus, when the polishing compound is initially placed within the interior 60, the polishing compound does not readily flow along the sidewall 62.

When the prophy cup 10 is rotated about the central axis 2, a centrifugal force F is exerted on the polishing compound along line F (FIG. 4). This force F acts substantially horizontally and perpendicular to the central axis 2. It is noted that the centrifugal force F is actually a reactionary force to a centripetal force (equal and opposite to the force F) applied by the sidewall 62 of the prophy cup 10 to cause the polishing compound to remain a constant distance from the central axis 2 during rotation.

Because the sidewall 62 diverges slightly away from the central axis 2, as the sidewall 62 extends from the floor 64 to the rim 50, a component of the centrifugal force F acts along the sidewall 62 and toward the rim 50. This component force P acting parallel to the sidewall 62 is counteracted only by the friction between the polishing compound and the sidewall 62. Once this friction force is overcome, the polishing compound is flung out of the interior 60 of the prophy cup 10.

The projections 70, having line segments 71 with an orientation non-coplanar with the central axis 2, resist this force parallel to the sidewall 62. The various regions 73, 80 formed by the projections 70 provide varying levels of resistance to polishing compound migration along the sidewall 62. It is noted that when the projections 70 are arranged in a diamond-like pattern, that polishing compound migration resistance is identical regardless of a direction of rotation of the prophy cup 10. Other, non-biased patterns of line segments 71 could also be utilized which would exhibit consistent performance regardless of the direction of rotation of the prophy cup 10.

Areas between adjacent projections 70 and below gaps 78 form the impoundment regions 80. The impoundment regions 80 do not totally isolate the polishing compound 80 from migrating along the sidewall 62, through the associated gap 78 and toward the rim 50. However, the gaps 78 cause a bottleneck effect by having a lesser width than portions of the impoundment region 80 adjacent the floor 64. The impoundment region 80 thus meters the polishing compound 80 along the sidewall 62. The polishing compound within the impoundment region 80 migrates up the sidewall 62 at a lesser rate than it would without the impoundment region 80 and gap 78 between the projections 70.

Each projection 70 surrounds an associated confinement region 73. Polishing compound within the confinement region 73 is inhibited from migrating parallel to the sidewall 62 and toward the rim 50. For the polishing compound to migrate out of the confinement region 73, the polishing compound must build up against the resistance side 75 of the line segments 71 of the projection 70 surrounding the confinement region 73 until the polishing compound can climb over the crest 76 of the projection 70. The projection 70 surrounding the confinement region 73 thus provides polishing compound metering at a rate which is generally slower in metering out polishing compound than the impoundment region 80 below the gap 78.

A rate of flow of polishing compound out of the confinement region 73 and impoundment region 80 is also impacted by the presence of water and other fluids within the environment in which the prophy cup 10 is utilized. When the interior 60 is initially filled with polishing compound, the interior is often less filled with water and saliva than it is once the prophy cup 10 is located within the mouth of a patient. Once the polishing process begins and the interior 80 is located adjacent a tooth or other dental structure, saliva impacts the sidewall 62 and polishing compound causing the polishing compound to become less viscous. The polishing compound then more easily migrates out of the confinement region 73 and the impoundment region 80.

In addition, when the prophy cup 10 is applied against the dental structures with pressure, the side wall 62 is splayed outward radially somewhat. This action increases the magnitude of the component force P parallel to the sidewall 62 and exposes the polishing compound within the regions 73, 80 more directly to the dental structures for use thereon. As a result, the polishing compound is held more securely within the interior 60 by the projections 70 before utilization in polishing a tooth or dental structure. One utilization begins, the polishing compound is metered out of the interior 60 over a finite period of time.

Initially, the polishing compound not contained within either the confinement region 73 or the impoundment region 80 would most likely exit the interior 60. The polishing compound within the impoundment region 80 can then be metered out of the interior 60. Finally, the polishing compound within the confinement region 73 can be metered out of the interior 60 for use in polishing teeth and dental structures. Polishing compound is not disposed in too great an amount initially and only gradually empties out of the interior 60. Thus, less polishing compound is wasted and the interior 60 maintains a supply of polishing compound for a longer period, requiring fewer refilling steps of the interior 60.

While using the prophy cup 10, a dental professional would initially locate the prophy cup 10 upon a prophy angle D such as a disposable prophy angle which is operatively connected to a dental handpiece. The prophy cup 10 would then be located near a supply of polishing compound and the interior 60 of the prophy cup 10 would be filled with polishing compound. Once the interior 60 has been filled with polishing compound, the prophy cup 10 can be rotated with less risk of migration of polishing compound out of the interior 60 before the interior 60 impacts the dental structures.

Alternatively, the prophy cup 10 can be located adjacent to the dental structures first before rotation of the prophy cup 10. In either case, the polishing compound is held within the interior 60 for a greater period of time and is metered out more consistently from the interior outward for use with the dental structures. The polishing compound is then metered out of the interior 60 until the interior is empty. The interior 60 is then refilled and the process continues.

In an alternative embodiment, shown in FIGS. 7 and 8, a prophy cup 110 is provided similar to the prophy cup 10 except with a distinctive means for attachment to the prophy angle D. Specifically, the bottom surface 130 includes a threaded shaft 120 extending therefrom with threads 122 thereon. The threads 122 are formed complemental to a threaded hole in a prophy angle. While the prophy cup 110 reveals on alternative attachment means, other attachment means, such as a threaded hole in the bottom surface 130, are also contemplated.

In a second alternative embodiment, shown in FIGS. 9 and 10, a prophy cup 210 is provided similar to the prophy cup 10 except with another distinctive means for attachment to the prophy angle D. Specifically, a cylindrical shaft 220 depends perpendicularly from the bottom surface 230. The cylindrical shaft 220 includes a cylindrical recess 222 near a tip 224 of the shaft 220. The cylindrical recess 222 circumscribes the shaft 220 and defines a lesser diameter necked down portion of the shaft 220. The recess 222 forms a latch coupleable to a complementally formed rotating shaft commonly found on contra-angle prophies in a manner similar to the prophy cups 10, 110.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A dental prophylaxis cup for applying polishing compound to dental structures comprising in combination:

a cup having a bottom surface on a first end including an attachment means, and a second end opposite said first end including a concave interior region defined by a sidewall extending from a floor to a rim;

a plurality of projections extending from said sidewall, said projections including means for restraining release of polishing compound from within said interior region;

said restraining means including segments of said projections converging toward each other as said segments extend toward said rim, said restraining means including a plurality of recesses in said sidewall, each said recess contained by line segments which project up from said sidewall, said line segments circumscribing and defining said recess.

2. The device of claim 1 wherein said restraining means includes projections spaced from each other by a gap, said gap decreasing in size as the projections extend from said floor to said rim, forming an impoundment region bounded on one side by said floor, two sides by said projections, and one side by said gap, whereby release of the polishing compound occurs in a metered fashion through a bottleneck formed by said gap.

3. The device of claim 2 wherein said restraining means includes said projections oriented to form confinement regions defining said recesses, each of said confinement regions forming an enclosed boundary entirely circumscribed by said projections.

4. The device of claim 1 wherein said rim of said second end is substantially circular and wherein said floor is substantially circular, and wherein a diameter of said rim is greater than a diameter of said floor.

5. The device of claim 1 wherein said sidewall is formed from an elastomeric substance providing a means for the sidewall to deform upon impact with dental structures.

6. The device of claim 5 wherein each of said projections are oriented to form a polygonal shape with a confinement region defining one of said recesses between attached line segments of each said projection, said confinement region completely surrounded by said line segments, and said impoundment region is formed between unattached adjacent said projections.

7. The device of claim 6 wherein said projections include a leg extending from said confinement region to said floor, whereby adjacent said impoundment regions are segregated, and wherein said unattached adjacent projections have a gap therebetween, said gap having a width less than a maximum distance between said legs of said unattached adjacent projections.

8. The device of claim 1 wherein said attachment means of said first end is an orifice having a greater width region above a lessor width neck, said orifice sized to receive a complementally formed protuberance operatively coupled to a dental handpiece, whereby said cup is rotationally attached to the dental handpiece.

9. The device of claim 1 wherein said attachment means is a threaded shaft extending from said first end, said threaded shaft having a configuration complemental to a threaded opening operatively coupled to the dental handpiece.

10. A dental prophylaxis polishing compound dispensing device which is coupleable to a dental handpiece, the device comprising in combination:

a cup having an attachment end and a dispensing end, said attachment end including means for attaching to the dental handpiece in a rotatably supportable manner, such that rotational force supplied by the dental handpiece is transmitted to said cup, and a polishing compound retention surface upon said dispensing end, said retention surface including means to resist centrifugal force applied to the polishing compound by rotation of said cup;

said resistance means including confinement regions formed by projections extending from said retention surface and interposed between said confinement regions and a rim of said retention surface, said resistance means including a plurality of recesses in said retention surface, each said recess bounded by line segments of said projections extending from said retention surfaces, said line segments surrounding said recess and said recess having an open top on a side of said recess opposite said retention surface said open top including means to provide access between said recess and said dispensing end of said cup, whereby when polishing compound is applied to said retention surface and said cup is rotated, said retention surface resists release of the polishing compound.

11. The device of claim 10 wherein said retention surface is a concave depression with sidewalls extending away from said attachment end.

12. The device of claim 11 wherein said cup is radially symmetrical with a central axis of said concave depression co-extensive with the axis of rotation of said cup.

13. The device of claim 10 wherein said retention surface includes sidewalls., and said centrifugal force resistance means is a plurality of said projections on said sidewalls of said retention surface surrounding said confinement regions.

14. The device of claim 10 wherein said projections include a resistance side which is not coplanar with an axis of rotation of said cup, whereby said resistance side inhibits the centrifugal force applied to the polishing compound.

15. The device of claim 10 wherein said retention surface includes sidewalls, and said projections extend in line segments, each line segment defined by a crest spaced from a sidewall by a resistance side.

16. The device of claim 15 wherein said line segments are grouped to form said confinement regions entirely surrounded by said line segments.

17. The device of claim 10 wherein said retention surface includes sidewalls, and said cup is formed from flexible elastomeric material to allow said sidewalls of said retention surface to flex radially outward away from said axis of rotation.

18. A method for applying polishing compound to dental structures of an individual and polishing the dental structures, including the steps of:

providing a prophy cup having an attachment end attachable to a prophy angle, the prophy angle in turn attachable to a dental handpiece in a manner supplying rotation from the dental handpiece to the cup, and a dispensing end with a polishing compound retention surface, the retention surface provided with a plurality of recesses in the retention surface, each recess bounded by line segments extending from the retention surface, the line segments surrounding the recess and the recess having an open top on a side of the recess opposite the retention surface, the open top including a means to provide access between the recess and the dispensing end of the cup;

filling the dispensing end of the prophy cup with polishing compound;

applying a portion of the polishing compound, not adjacent the retention surface, to the dental structure to be polished;

rotating the prophy cup;

polishing the dental structure with the dispensing end of the prophy cup; and metering flow of a portion of the polishing compound, adjacent the retention surface, into contact with the dental structures;

whereby polishing compound is provided within the prophy cup for an extended period of time without repeating said filling step.

19. The method of claim 18 wherein said providing step includes the step of establishing impoundment regions between projections extending from the polishing compound retention surface, the projections surrounding the impoundment regions except where gaps are provided allowing polishing compound to escape therethrough.

20. The method of claim 19 wherein said providing step includes the step of establishing confinement regions totally surrounded by the projections such that the polishing compound must climb over a crest of the projections to accomplish displacement from the confinement regions.

21. A dental prophylaxis cup for applying polishing compound to dental structures comprising in combination:

a cup having a bottom surface on a first end including an attachment means, and a second end opposite said first end including a concave interior region defined by a sidewall extending from a floor to a rim;

a means for restraining release of polishing compound from within said interior region;

said restraining means including a plurality of recesses in said sidewall, each said recess defined by line segments which circumscribe said recess, said line segments projecting up from said sidewall.

* * * * *